United States Patent [19]
Kroll et al.

[11] Patent Number: 4,763,660
[45] Date of Patent: Aug. 16, 1988

[54] FLEXIBLE AND DISPOSABLE ELECTRODE BELT DEVICE

[75] Inventors: Mark W. Kroll, Rogers; Mark R. Pommrehn, Bloomington; Dan Hanson, Minneapolis, all of Minn.

[73] Assignee: Cherne Industries, Inc., Minneapolis, Minn.

[21] Appl. No.: 24,919

[22] Filed: Mar. 13, 1987

Related U.S. Application Data

[63] Continuation of Ser. No. 807,346, Dec. 10, 1985, abandoned.

[51] Int. Cl.$^4$ .............................................. A61B 5/04
[52] U.S. Cl. .................................. 128/640; 128/644; 128/798; 439/77
[58] Field of Search .............................. 128/639–641, 128/644, 798, 802, 803; 339/17 F; 439/77

[56] References Cited

U.S. PATENT DOCUMENTS

| | | | |
|---|---|---|---|
| 4,365,634 | 12/1982 | Bare et al. | 128/640 |
| 4,442,315 | 4/1984 | Segawa | 128/639 |
| 4,477,137 | 10/1984 | Ayer | 339/17 F X |
| 4,583,549 | 4/1986 | Manoli | 128/640 |

FOREIGN PATENT DOCUMENTS 2735050  2/1979  Fed. Rep. of Germany ...... 128/640

OTHER PUBLICATIONS

Petrucelli et al., "A Serial to Parallel ... Suppression", Proc. New Eng. Bioeng. Conf., 22-23, Nov. 1979, Troy, N.Y., pp. 388-390.

*Primary Examiner*—Lee S. Cohen
*Attorney, Agent, or Firm*—Anthony G. Eggink

[57] ABSTRACT

The unitary flexible and disposable electrode belt and method is for receiving and transmitting electric current or voltage for use on the body of a patient. The belt has a unitary layered body structure that is releasably secured to the patient. The belt device body structure has a terminal end that is connectable for communication with medical therapeutic and diagnostic apparatus. The layered body structure further includes a plurality of flexible non-conductive and conductive layers, a conductive network having electrode contact areas at predetermined positions and conductive adhesive members to removably hold the device to a patient and to, thereby, transfer electrical signals between predetermined patient body locations and the medical therapeutic and diagnostic apparatus.

26 Claims, 6 Drawing Sheets

FLEXIBLE AND DISPOSABLE ELECTRODE BELT DEVICE

This is a continuation of application Ser. No. 06/807,346, filed 12/10/85, now abandoned.

BACKGROUND OF THE INVENTION

This invention relates to a device and method for receiving and transmitting electrical signals to and from a patient. Particularly, this invention relates to a disposable, flexible and layered electrode belt, also referred to as a "belt", for placement and use on the body of a patient and also for use with medical diagnostic and therapeutic devices.

The belt according to this invention is useful in providing a disposable and flexible layered structure which quickly and easily adheres to the skin of a patient and which is operative on the patient at predetermined locations. The thin flexible belt provides a patient body contour conforming structure which is in direct conductive electrical communication to permit the transmission of a broad range of electrical signals.

The belt of the invention further permits medical personnel to inexpensively, efficiently, accurately, aseptically and removably affix the belt device to predetermined body locations of the patient. The device provides means to receive bioelectric signals from predetermined anatomical locations for subsequent or simultaneous analysis on diagnostic equipment, such as cardiac analyzers, and to transmit an electric current or voltage to specific anatomical locations for therapeutic purposes. The device is usable on the chest, back, head and limbs of the patient and is also usable simultaneously on the patient's chest and back areas, for example, for various diagnostic and therapeutic purposes.

The flexible electrode belt device and method of this invention provides a means to introduce a plurality of electrode elements for communication with the body of the patient for purposes of sensing bioelectric signals, introducing an electric current or voltage at predetermined locations on the body of the patient, or for both of these purposes simultaneously. Thus, the electrode belt is provided to obtain bioelectric data for use in cardiac or other analyzers or for therapeutic purposes.

The electrode belt of the invention is a flexible unitary composite of layered materials which resists entanglement, is easy to manipulate and may be quickly and accurately affixed to the contours of a patient body. The electrode belt of the invention significantly reduces the number of steps and time required to perform medical diagnostic and therapeutic functions because the device is provided with conductive adhesive electrode surfaces, with reference means for positioning the device on the patient and with electrodes that are positioned at predetermined locations in the device.

The belt device is also adaptable to permit the positioning of electrodes at locations outside the predetermined positions on the device. For example, the device may be adjusted to place electrodes at standard EKG limb electrode locations. The belt device is thin and flexible and it conforms to the contours of an individual patient's body for accuracy. The thin configuration of the device also reduces material usage in manufacture and provides an electrode belt that is cost effective.

The invention further provides an electrode belt device that is disposable, which is an improvement over prior art devices which typically require much maintenance and care. Additionally, its disposability is particularly beneficial in a medical setting, wherein the possibility of transfer of communicable diseases from patient to patient is of great concern. Because the belt device and its components are designed for individual patient use, risks that are inherent in multiple patient use devices are minimized.

In the past, several types of electrode devices have been utilized or proposed for use with electro/medical analyzers, such as electrocardiograph instruments. These devices have, however, been limited in signal pickup and placement function and have generally been designed for use with these specific types of analyzer instruments. Additionally, various types of layered devices have been proposed for use in the medical industry which are designed for use with specific forms or types of insertable and reusable electrode elements. And, still others have been provided which do not fit to the human body contours and which thus limits their effective signal transmissions.

These prior art devices have generally been costly to manufacture or have been designed for repeated use and, thus, present the possibility of transmitting communicable diseases. Still other devices have proposed electrode placements which make them unsuitable and cumbersome for any other medical analyzing purposes.

The flexible and disposable electrode belt of this invention overcomes the limitations, difficulties and shortcomings of these prior art devices. The device in accordance with the teachings of this invention provides a versatile, functional, inexpensive, aseptic and easy to use disposable and flexible electrode belt for use by medical personnel in conjunction with medical diagnostic and therapeutic equipment that utilizes bioelectric signal inputs or electric outputs. And, despite the longstanding need for such a device in the medical diagnostic and therapeutic area, none in so far as is known has been developed.

SUMMARY OF THE INVENTION

The invention provides a flexible and disposable belt device for the releaseable securement to the body of a patient and for receiving and transmitting electric current and voltage. The belt has a composite and layered body structure with a terminal end which is connectable for use with a cable set of a medical therapeutic and diagnostic apparatus.

The flexible and layered body structure has a flexible non-conductive base structure layer for supporting and electrically insulating the remaining elements of the composite and layered body structure. A conduction network is affixed to the nonconductive base layer and has a plurality of predetermined contact areas for receiving and transmitting electrical signals and a signal distribution system extending from the contact areas to the terminal end of the device.

The flexible and disposable belt device is further provided with an inner non-conductive insulation layer which is affixed and coextensively disposed to the non-conductive base layer for insulating the signal distribution system from the body of a patient. The inner nonconductive layer has a plurality of predetermined apertures for exposing the conduction network contact areas, and has a void area at the terminal end for exposing the signal distribution system.

Conductive adhesive members are affixed and coextensively disposed at each predetermined aperture of the inner insulation layer for communicating with the contact areas and the body of a patient, for transferring electrical signals therebetween and for holding the device to the patient.

Further provided by the disposable electrode belt device is at least one conductive shielding layer that is coextensively affixed to the non-conductive base layer for reducing interference with and from the remaining elements of the body structure, and for the electrical grounding of the device. Each conductive shielding layer is separated by a non-conductive layer. Each shielding layer is peripherally recessed with respect to each non-conductive layer to minimize the risk of shorting and patient shock due to device or medical diagnostic and therapeutic apparatus malfunction.

Also provided by this invention are belt device body structures having separable side portions defined by separation means disposed at predetermined longitudinally extending locations. The separation means are disposed within and between the conduction network, and one or more contact areas within the separable side portions are extendable outwardly from the device body structure. The body structure is also provided with anatomical placement reference means to coordinate the contact areas relative to predetermined body locations of a patient.

Also provided by the invention are device embodiments having reusable and disposable portions, electrode belt body structures constructed of particular flexible materials and having predetermined contact areas for specific applications.

Finally, provided by this invention are methods for receiving and transmitting electric current and voltage to a patient which involve specific steps as well as the use of particular flexible and disposable electrode belt device embodiments for certain uses.

These and other benefits of this invention will become clear from the following description, by reference to the drawings.

DESCRIPTION OF THE PREFERRED EMBODIMENTS

Figure 1:
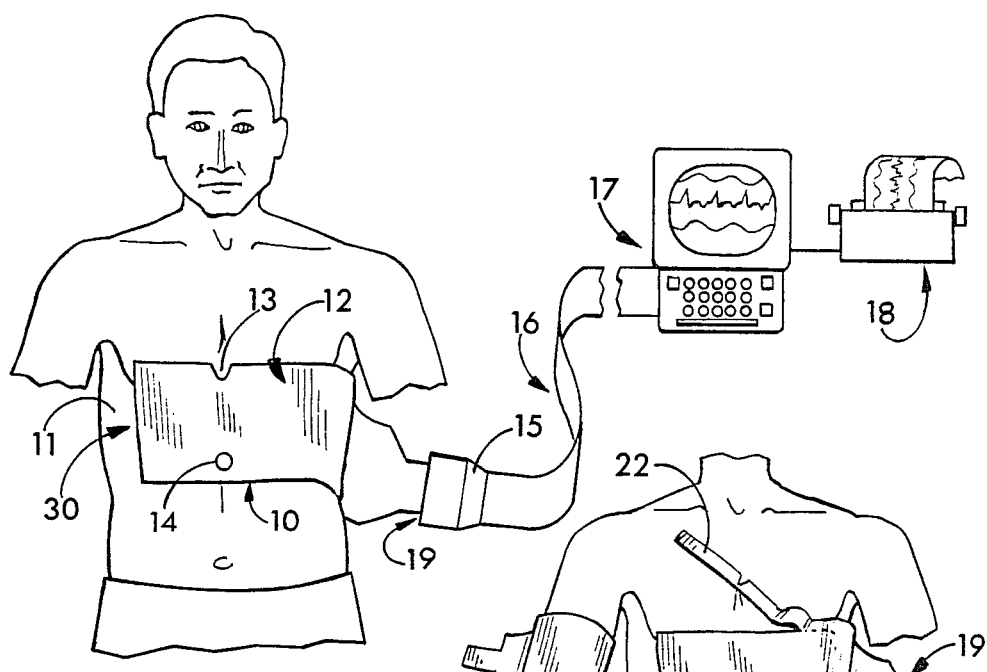
FIG. 1 is a frontal view of the flexible and disposable electrode belt of this invention shown in an operative position on the chest of a patient.

FIG. 1 shows the flexible and disposable electrode belt 10 in an operative position on the precordial region of a patient 11. It is comprised of a body structure 12 which has a proximal end 30 and a terminal end 19. A pair of anatomical alignment means 13 and 14 are located at its proximal end 30. The flexible and disposable electrode belt 10 is used to receive and transmit an electric current or voltage from and to the body of a patient.

The terminal end 19 of the body structure 12 of belt 10 is connectable to a connector 15 of a cable set 16 of a complementary diagnostic or therapeutic device 17. Additionally, as is shown in FIG. 1, the device 17 may be communicatively linked to a printer 18 to receive hard copy.

Figure 2:
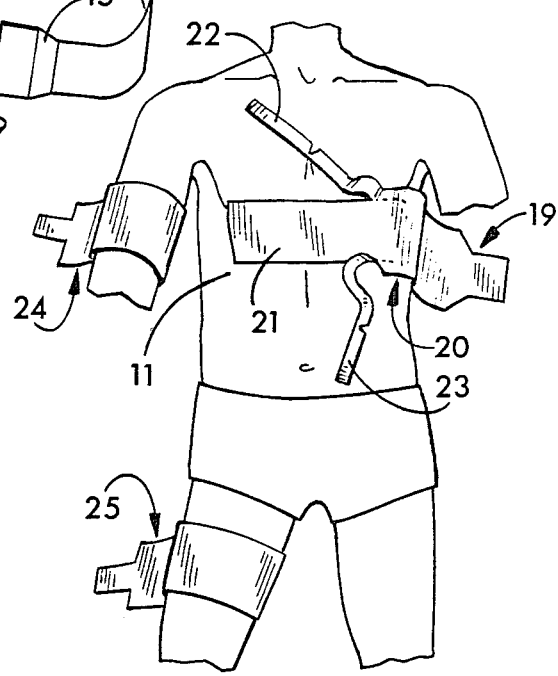
FIG. 2 is a frontal view of another embodiment of the present invention also shown in an operative position on the chest of a patient with its extendable side members fully extended and which also shows yet another embodiment of the belt in an operative position on the arm and leg of the patient.
Figure 3:
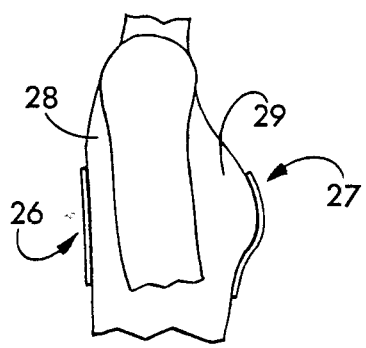
FIG. 3 is a view of yet another embodiment of the present invention where the electrode belt is shown placed both on the chest and back skin surfaces of a female patient.

FIG. 2 shows other embodiments of the flexible and disposable electrode belt 20, 24 and 25. The adjustable belt 20 has extendable side members 22 partially separable from the main body 21 for placement at locations outside the precordial region of a patient 11. Alternate embodiments of the belt 24 and 25 may be placed on the limbs or other parts of the body of a patient for various therapeutic and diagnostic purposes. FIG. 3 shows the belts 26 and 27 used simultaneously on the chest 29 and back 28 of a patient to receive and transmit electric current or voltage.

Figure 4:
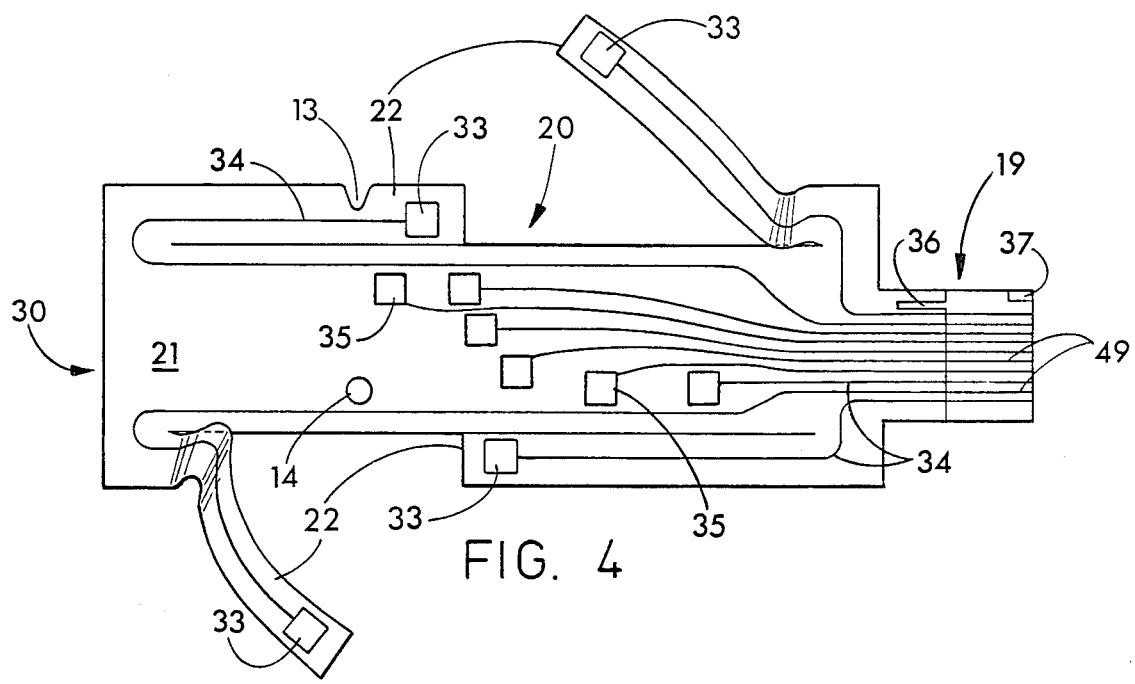
FIG. 4 is a plan view of the presnet invention illustrating its patient contact surface and showing a predetermined electrode positioning pattern, and further showing two side members extending from its main body structure.

FIG. 4 shows the flexible and disposable electrode belt 20 having a generally rectilinear, layered, composite main body 21 with a proximal end 30 and a terminal end 19. Located at the proximal end 30 of the belt 20 are a number of electrodes 35. Anatomical alignment means 13 are disposed on the top lateral edges of the device 20. The alignment means 13 and 14 are a notch 13 or aperture 14 through all layers of the device 20 or printed reference lines or the like. Anatomical reference aperture 14 is specifically designed for alignment with the xiphoid process.

Disposed toward the lateral edges of the proximal end 30 of the main body 21 are adjustable side members 22. The side members 22 consist of a layered, composite structure of the same elements of which the main body 21 is constructed, affixed to the main body 21 permanently at one end. They may be removably affixed by translayer perforations on at least one lateral edge or loose as shown, i.e., as having previously been cut during manufacture. Each side member 22 contains an electrode 33.

Both the main body and side member electrodes 35, 33 transmit and receive electric signals to and from the terminal end 19 of the belt 20 by way of a current distribution member or lead strip 34. The lead strips 34 and electrode portions, discussed below, are of a flexible conductive ink compound having a conductive filler having Silver, Aluminum, or compounds thereof, or of a similarly suitable material. Preferably, the ink deposit is of a preselected conductivity to provide a certain total lead strip resistance so that each strip 34 serves as a current limiter to protect a patient from shock due to malfunction of the device 20 or of a complementary medical device. A conductive filler composition resulting in a lead strip resistance of approximately 1000 ohms allows for signals transmission throughout the lead strip 34 and also providing the above-mentioned current limiter qualities as is prefered for this invention. The lead strips 34 extend from each electrode 33, 35 to the terminal end 19, where they are aligned generally in a parallel fashion as shown by leads 49 and are uniformly spaced apart approximately 0.050 inch.

Figure 5:
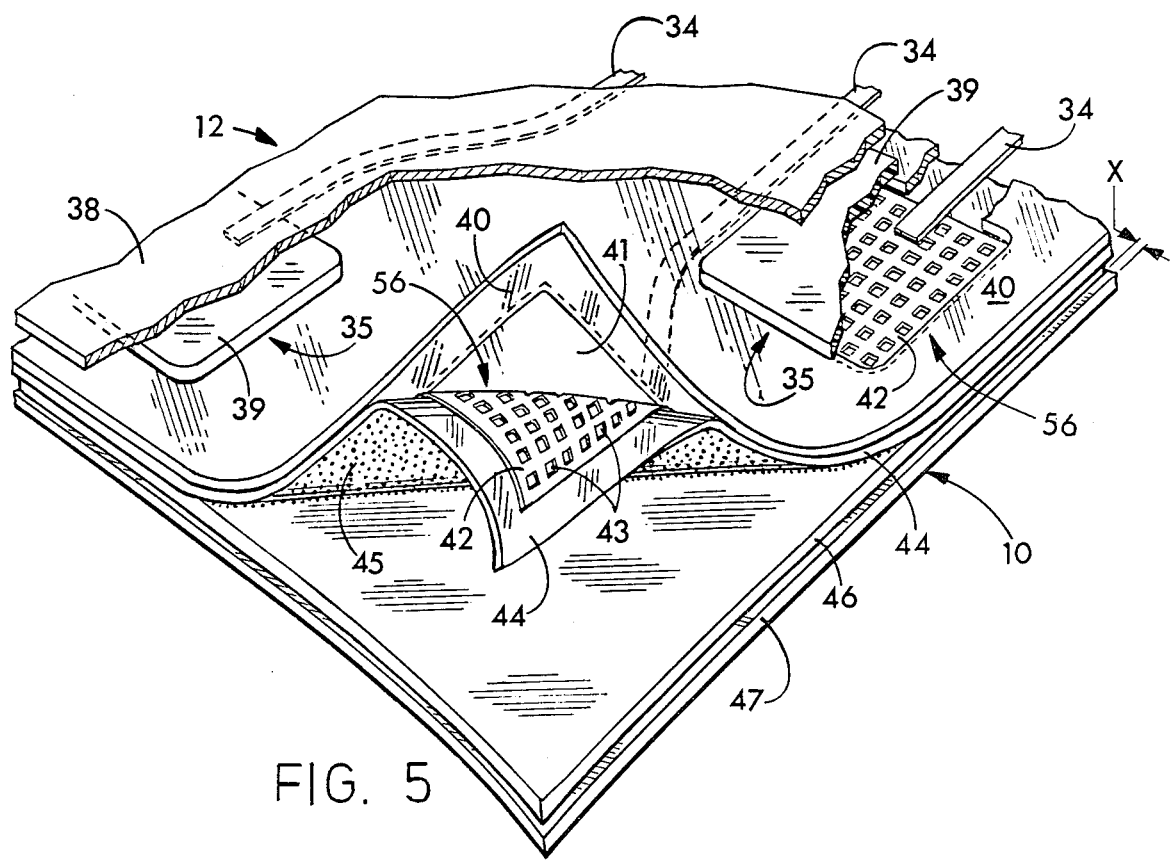
FIG. 5 is a partial perspective view of the layered structure of the invention having a corner portion peeled back for clarity, and being partially in section to show its elements.
Figure 6:
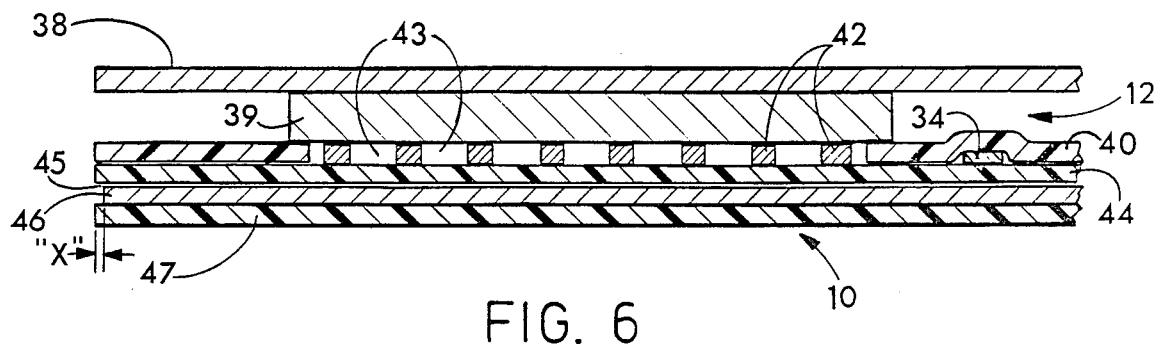
FIG. 6 is a cross-sectional view of the present invention which illustrates its layered body structure.

Referring to FIGS. 5 and 6, the belt 10 is illustrated to have a plurality of electrodes 35. Each electrode 35 has a conductive grid 56 which is comprised of a matrix of approximately 0.050 inch wide lines 42 of conductive ink compound applied to an insulation and base support layer 44 preferably by means of a silk screen process. The conductive ink is a silver compound generally used in the electronics industry. Each matrix line is approximately 0.050 inch wide. This width is optimal for good conductivity. The conductive ink compound used in the matrix lines 42 is generally the same as that utilized in the lead strips 34. Apertures 43 in the conductive ink matrix 42 form the grid configuration. The grid configuration itself is provided both for proper electrical function as well as to reduce the amount of ink used while obtaining maximum function. The insulation and base support layer 44 is preferably comprised of a thin approximately 0.001 inch polyester laminate and serves as both a base for the silk screened conductive ink used in the matrix lines 42 and lead strips 34, and as an electrical insulator.

Another component of the electrode 35 is an aperture 41 in an inner patient insulation layer 40. The inner patient insulation layer 40 has a thin non-conductive sheet of polyester coextensive with and bonded to the insulation and base support layer 44. Bonding may be accomplished by an adhesive or a lamination process. It serves to insulate the patient's skin from electric current or voltage in the electrode lead strips 34. The inner patient insulation layer aperture 41 is provided to expose the conductive grid 56 for contact.

As is further shown, conductive gel pads 39 are provided as conductive interfaces between the conductive grids 56 and a patient's skin. The gel pads 39 are provided to make contact with a patient's skin rather than having direct contact with the conductive ink because the latter provides a less reliable signal or input. Moisture from the skin in direct contact with the electrode may cause changes in conductivity and, therefore, may lead to erroneous bioelectric data. The gel pads 39 maintain direct electrical contact with the skin, to reduce variations in conductance, and it permits this contact for long periods of time. The gel pad 39 is a conductive, gelatinous compound which also has adhesive properties for contoured adhesion to the body of a patient and the communicating portions of the belt body structure. Compounds having these characteristics have been developed by Minnesota Mining and Manufacturing, Medtronic Inc. and Lec Tec (Synkara TM), corporations that are located in Minnesota, U.S.A. Generally, these compounds are gelatenous, have adhesive qualities and have low resistivities. Each gel pad 39 is placed in such a position so as to cover and fill into the entire inner patient insulation layer aperture 41. For example, gel pad 39 generally fills the apertures 43 in the grid electrode configuration 42, shown in FIG. 6. Alternatively, a layer of the conductive, adhesive gel, generally coextensive with the proximal end 30 of the body 12 of the device 10 may be used, for example, gel layer 53 in FIGS. 11 and 12. The gel pad 39 has a pressuresensitive, moisture resistant adhesive property which causes the entire belt 10 to adhere to a patient's skin, thus obviating the need for cumbersome straps or other retainers.

The elements of the belt 10 described heretofore are shielded from outside electrical interference by a shielding layer 46. The shielding layer 46 also prevents interference from the device 10 with other medical diagnostic and therapeutic devices. The shielding layer 46, in addition to being a general static shield, also serves to ground the belt 10. It is comprised of a conductive substance such as a silver or aluminum composition, for example. In the present invention, the shielding layer 46 is preferably thin and is generally coextensive with and bonded to the insulation and base support layer 44. Bonding may be accomplished by a non-conductive adhesive layer 45 of a standard acrylic adhesive composition, for example, permanently applied to the outer side of the insulation and base support layer 44, or by a lamination process.

The composite layers of the device 10 effectively form a capacitor comprising a first plate, a second plate and a dielectric. The first plate is the conductive grid 56. The shielding layer 46 acts as the second plate while the insulation and base support layer 44 acts as the dielectric between the wo plates. These three elements of the device 10 in conjunction with the gel pad 39 resistance and a patient's skin resistance provide a low pass filter which shunts high frequency interference to ground. The effectiveness of this configuration is dependent upon grid 56 dimensions which have optimally been found to be about 1 inch square in conjunction with an approximately 1 mil. thick insulation layer.

The shielding layer 46 is bonded to an outer insulation layer 47 that is generally coextensive therewith. The outer insulation layer 47 is comprised of a non-conductive polyester laminate, for example. The outer insulation layer 47 serves, generally, to protect the integrity of the other elements of the belt 10. In the preferred embodiment, the shielding layer 46 is metalized to the outer insulation layer 47, but bonding may be made by an adhesive or by a lamination process. Alternatively, it is within the purview of this invention to have the shielding layer 46 directly deposited onto the base support layer 44, a process known in the art.

Figure 13:
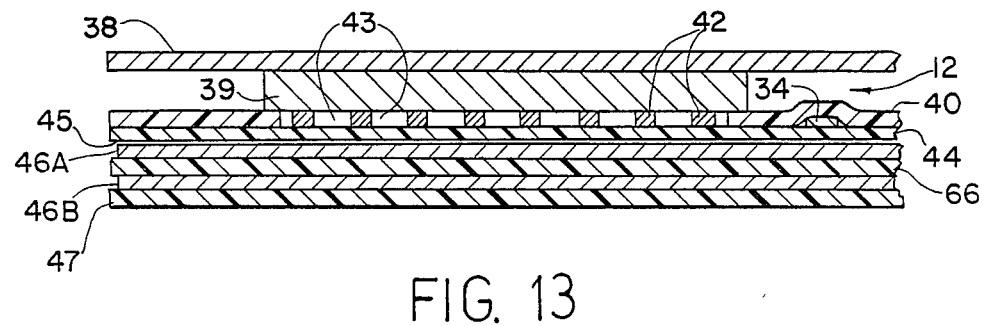
FIG. 13 is a cross-sectional view of an embodiment of the present invention which illustrates multiple shielding layers in its body structure.

It is within the purview of this invention to have more than one shielding layer 46 to further shield the device from interference. FIG. 13 shows an embodiment of the device having multiple conductive shielding layers 46A and 46B. The shielding layers 46A and 46B are separated from one another by a generally coextensive, non-conductive separation layer 66. The exterior layer 47 of the device, as discussed above, is the non-conductive outer insulation layer. Although two shielding layers 46A and 46B are shown in FIG. 13, this multiple shielded embodiment may similarly have more such layers if required.

The shielding layer 46 is preferably recessed inwardly at its outer boundaries to minimize the risk of electrical shorting and patient shock in the event of device 10 failure. In this configuration, insulation and base support layer 44 and outer insulation layer 47, instead of being coextensive with the shielding layer 46, overlap the shielding layer 46 slightly, approximately 0.1 inch for example, as shown by "X" in FIGS. 5 and 6, and thus permits the bonding of base support layer 44 to outer insulation layer 47 to further insulate the belt 10.

A sanitary release liner 38 is provided to protect the belt 10, particularly the patient contact surface of the gel pads 39, while in storage and during handling. It is generally coextensive with the shelding layer 46. The sanitary release liner 38 is comprised of a paper base which is preferably coated with silicone, or other similarly effective release agent, on one side for contact with the gel pads 39. The adhesivity of the gel pad 39 acting in concert with the coating allows the sanitary release liner 38 to adhere and re-adhere, subsequent to removal, to the body structure of belt 10.

Figure 7:
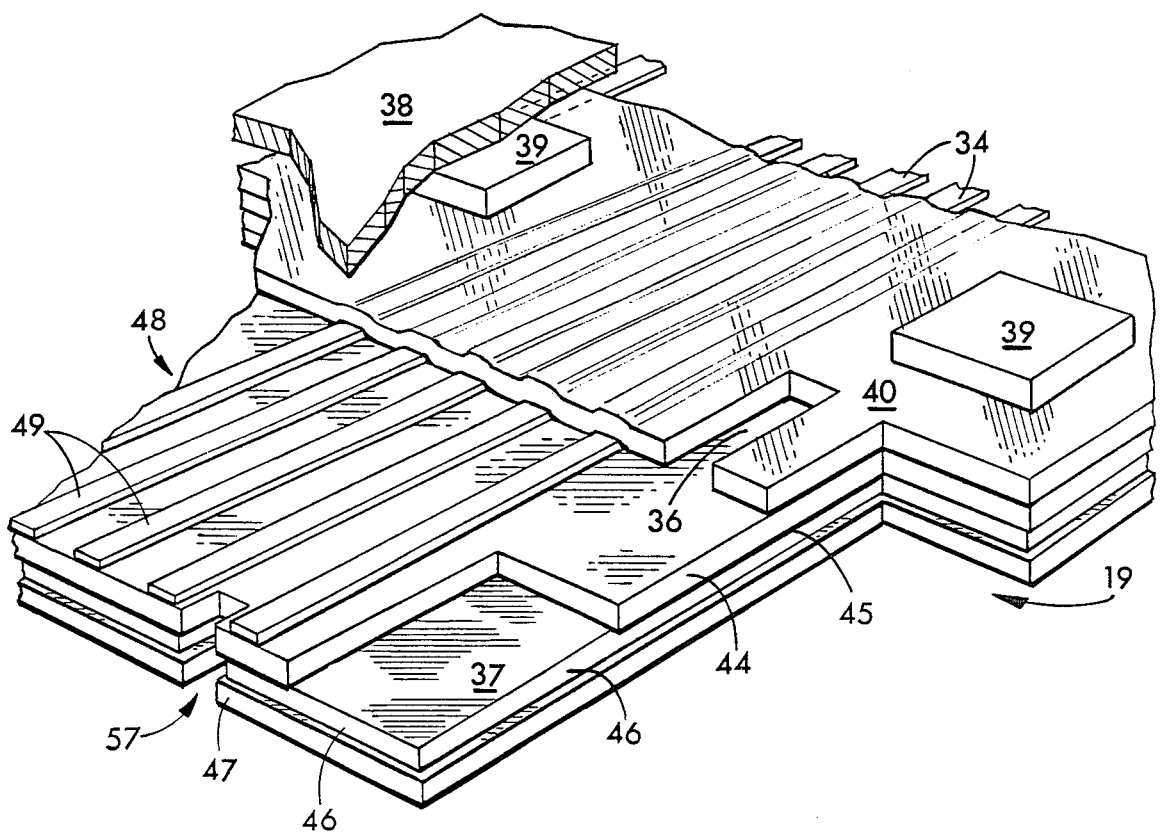
FIG. 7 is a perspective view of the terminal end of the present invention and which is shown enlarged for clarity.

FIG. 7 shows the terminal end 19 of the belt 10 in an expanded or exploded view. The terminal end 19 includes a rectilinear extention of the proximal end 30 of the main body 12 smaller in width than said proximal end 30 that is a composite of the various layers which comprise the main body 12 of the belt 10, an inner patient insulation layer terminal aperture 48, a passive polarization means 36, a ground contact 37, an active polarization means 57 and a plurality of exposed lead strips 49. These various elements cooperate generally to provide a terminal end 19 for hook up and communication with complementary medical devices.

The ground contact portion 37 is comprised of an exposed area, as shown in FIG. 7, of shielding layer 46 to expose the insulation and base support layer 44 and the adhesive layer 45. Thus, the exposed area 37 of the shielding layer 46 directly contacts a complementary ground connection of a medical device.

The inner patient insulation layer terminal void 48 is a terminal line of demarcation in the inner patient insulation layer 40 located approximately at the mid-point or intermediate in the length of the terminal end 19 itself such that the ground contact area 37, active polarization means 57 and the electrode lead strips 49 are exposed for contact with complementary elements of medical devices used in conjuntion therewith.

The passive and active polarization means 36 and 57 are provided to insure that the terminal end 19 is properly mated to its complementary medical device. In the preferred embodiment, the passive polarization means 36 is a channel in the inner patient insulation layer terminal 48 disposed toward one lateral edge of the terminal end 19 and extending into the inner patient insulation layer 40 exposing the insulation and base support layer 44 for visual inspection. It is provided to allow operator identification of the electrode lead strip 49 pattern for mating with complementary elements of medical devices used in conjunction with the device 10. The active polarization means 57 is provided to insure correct alignment of the exposed lead strips 49 with the above-mentioned complementary elements. It is preferably a notch in the terminal end 19 such that mating is impossible if the belt-to-connector orientation is reversed.

Figures 8, 9:
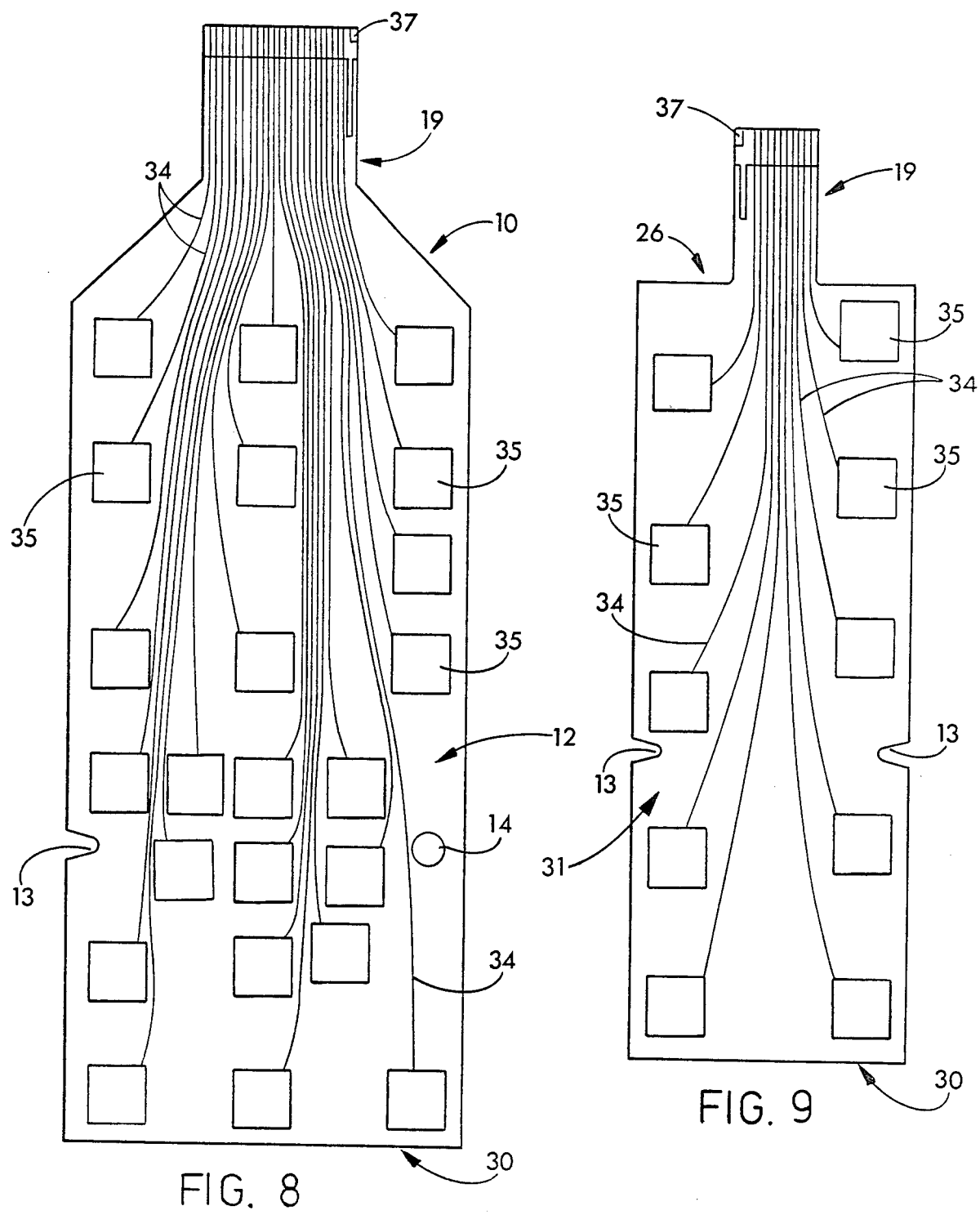
FIG. 8 is a plan view of the patient contact surface of the present invention showing a predetermined electrode positioning pattern.
FIG. 9 is a plan view of the patient contact surface of the present invention showing another predetermined electrode positioning pattern.

FIGS. 8 and 9 show predetermined electrode 35 locations on the flexible and disposable electrode belts 10 and 26 which are respectively designed for use on the precordial (FIG. 8) and back body (FIG. 9) portions of a patient. For example, the body structure of belt 10 is approximately $6\frac{1}{2} \times 15$ inches in size excluding its terminal end 19.

Figure 10:
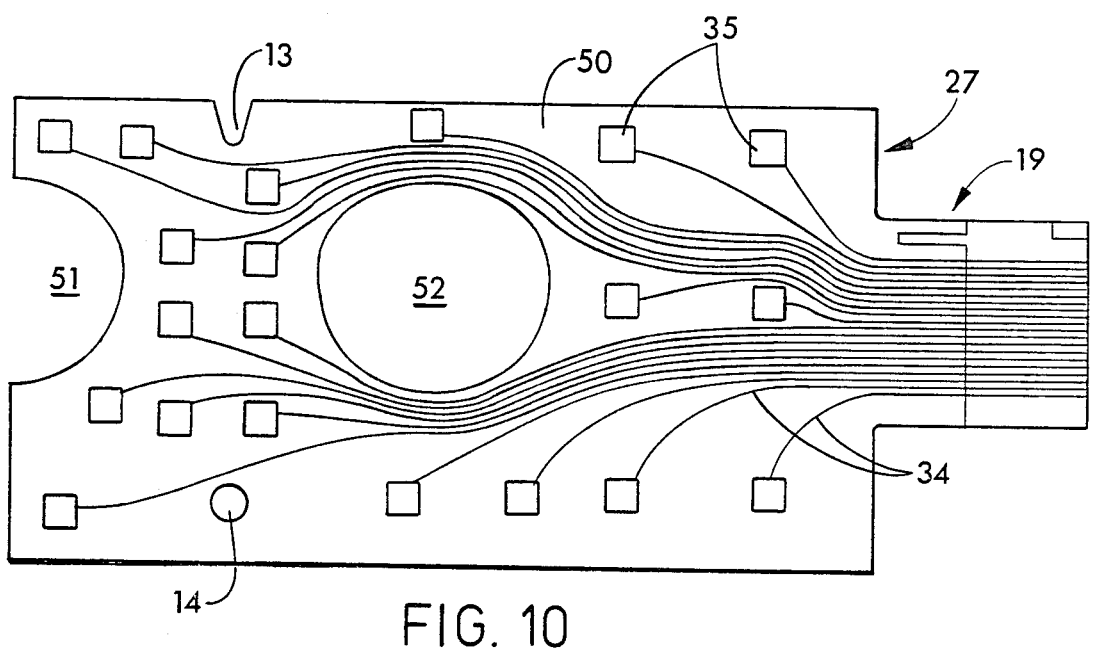
FIG. 10 is a plan view of the present invention showing an embodiment for use on the chest of a female patient.

FIG. 10 shows an embodiment of the flexible and disposable electrode belt 27 for use on the chest of a female patient. It has breast apertures 51 and 52 in its main body 50 as well as predetermined electrode 35 positions.

Figure 11:
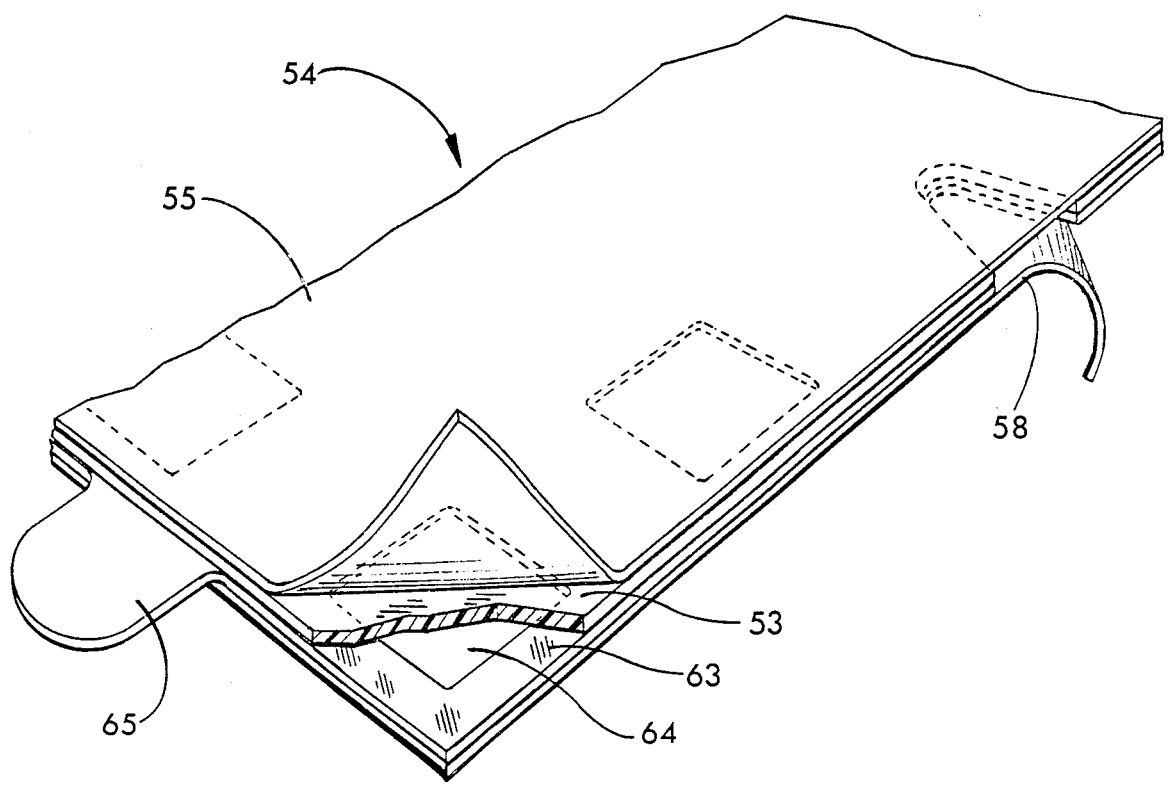
FIG. 11 is a partial perspective view of another embodiment of the invention showing a disposable component for use with a reusable component.
Figure 12:
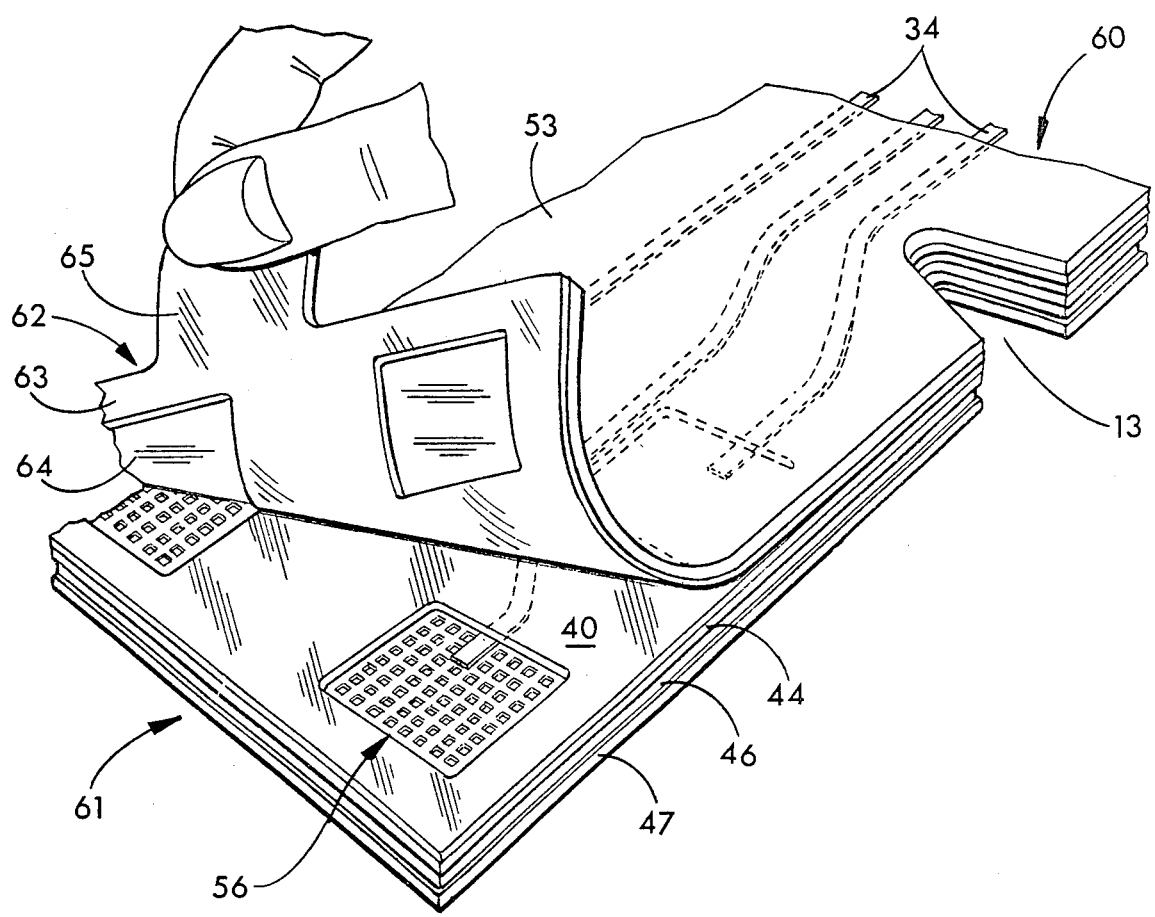
FIG. 12 is a partial perspective view of another embodiment of this invention showing a separated structure having reusable and disposable components.

A replacement patient interface structure 54 is shown in FIG. 11 and which is useable to produce a partly disposable structure 60 as shown in FIG. 12. The disposable structure 54 has release liners 55 and 58 attached to its opposing body sides to maintain asepsis and to protect it during storage. To attach the replacement patient interface structure 54 to a reusable portion 61 as shown in FIG. 12, liner 58 is removed. The exposed side of the patient interface structure 54 is then attached to the main structure 61 by aligning and placing the replacement patient interface structure 54 on the inner patient insulation layer 40 of the main structure 61. A slight pressure is then applied to either surface which will cause proper adhesion. The remaining sanitary release liner 55 is then removed to expose the conductive gel layer 53 and the device 60 is ready for another use.

FIG. 12 illustrates the flexible and disposable electrode belt 60 having a reusable portion 61 and the disposable portion 62 adhesively secured thereto. The reusable main structure 61 is comprised generally of the same elements as belt 10 shown in FIGS. 5 and 6 except for the conductive gel pads 39 and the release liner 38. The disposable structure 62 (patient interface structure 54 of FIG. 11 with liners 55 and 58 removed) is generally coextensive with the proximal end 30 of the belt 60 and is comprised of a main structure release layer 63 and a coextensive conductive adhesive gel layer 53. In use, the disposable patient interface structure 62 is placed so that its nonconductive main structure release layer 63 is in contact with the inner patient insulation layer 40 of the main structure 61. The patient interface structure 62 has apertures 64 at predetermined locations corresponding with the conductive ink grids 56 to expose the gel layer 53. The adhesive contact between the gel layer 53 and the conductive ink grids 56, therefore, serves to hold the main structure 61 and the patient interface structure 62 together during use.

The device 60 is used in generally the same way as the other embodiments previously discussed. It is placed on the body of a patient and attached to a therapeutic or diagnostic medical apparatus by removing the sanitary release liner 55 from the gel layer 53 of the patient interface structure 62.

Since adhesive contact is limited to certain specific locations, the two structures are easily separated subsequent to use on the body of a patient by lifting tab 65 of the patient interface structure 62. The patient interface structure 62 may then be disposed of. Thus, embodiment 60 allows for multiple uses of its main structure 61.

A method of receiving and transmitting electric current or voltage from and to a patient is also provided by this invention. Initially a set of patient body locations are selected for testing or treating purposes. A belt device 10 is provided having a body structure with electrode contact areas located therein to correspond with the set of predetermined patient body locations. After the sanitary release liner 38 is removed the belt structure is placed using its anatomical alignment means 13 and 14 to the patient's body.

The terminal end 19 of the belt 10 body structure 12 is matingly connected to connector 15 of cable set 16 of a diagnostic or therapeutic device 17. After the diagnostic or therapeutic procedure is performed, the belt device body is removed from the patient and discarded.

Although the electrode belts of this invention are disposable, it is within the purview of the invention to provide belt structures that have disposable portions which cooperate with reusable portion.

As shown by the belt embodiments of FIGS. 4, 8, 9 and 10, the belt of this invention, utilizing the flexible layered body structure and having the printed conduction network therein, permits a broad range of electrode 35 and electrode 33 placements so that a belt device can be easily manufactured to correspond with any predetermined patient body locations.

As many changes are possible to the embodiments of this invention utilizing the teachings thereof, the descriptions above, and the accompanying drawings should be interpreted in the illustrative and not in the limited sense.

That which is claimed is:

1. A unitary, disposable and flexible belt device for the releasable securement to the body of a patient and for receiving and transmitting electric current and voltage, said device having a composite and layered body structure with a terminal end and being connectable for use with a cable set of medical therapeutic and diagnostic apparatus, said composite and layered body structure further comprising:
   a. a flexible non-conductive base structure layer for supporting and insulating the remaining elements of said composite and layered body structure,
   b. a flexible conduction network affixed to said non-conductive base layer having a plurality of predetermined contact areas for receiving and transmitting electrical signals and a signal distribution system extending from said contact areas to the terminal end of the device, said signal distribution system and said contact areas of said flexible conduction network being comprised of a flexibly planar homogeneous layer of conductive material deposited on said base structure by a printing process,
   c. a flexible inner non-conductive insulation layer affixed and coextensively disposed to said non-conductive base layer for insulating said signal distribution system from the body of a patient, said inner non-conductive layer further having a plurality of predetermined apertures exposing said conduction network contact areas, and having a void area at said terminal end exposing said signal distribution system, and
   d. flexible conductive adhesive members affixed and coextensively disposed at each said plurality of predetermined apertures of said inner insulation layer for contact with said contact areas and the body of a patient to transfer electrical signals therebetween and for holding said device to the patient.

2. The device of claim 1, wherein a conductive shielding layer is generally coextensively affixed to said non-conductive base layer for reducing interference with and from the remaining elements of said body structure and for the electrical grounding of said device.

3. The device of claim 2, wherein said non-conductive base structure layer has at its terminal end a void exposing a portion of said conductive shielding layer for grounding purposes.

4. The device of claim 2, wherein said contact areas are of a predetermined size and further act in concert with said non-conductive base layer and said shielding layer to form a bypass capacitor to shunt high frequency interference to ground.

5. The device of claim 2, wherein said shielding layer is peripherally recessed with respect to said base structure layer to minimize the risk of shorting and patient shock due to device or medical diagnostic and therapeutic apparatus malfunction.

6. The device of claim 2, wherein an outer non-conductive insulation layer is affixed to said shielding layer.

7. The device of claim 2, wherein at least one additional shielding layer is generally coextensively affixed to said shielding layer closest said base structure layer to further shield said device from high frequency interference, said shielding layer and said additional shielding layer having a non-conductive separation layer affixed therebetween.

8. The device of claim 1, wherein said conductive adhesive members are extended and further affixed to one another thereby forming a single, homogeneous conductive and adhesive layer being generally coextensive with said inner insulation layer and said plurality of predetermined apertures of said inner insulation layer.

9. The device of claim 8, wherein said conductive, adhesive layer additionally has a release layer generally coextensively interposed between it and said inner insulation layer, said release layer further having the same said predetermined apertures at locations as said predetermined apertures of said inner insulation layer and further having a tab extending therefrom for allowing said conductive, adhesive layer and said release layer to be removed from the remaining elements of said device.

10. The device of claim 1, wherein said body structure has separable side portions defined by separation means disposed at predetermined longitudinally extending locations, said separation means disposed within and between said conduction network whereby one or more contact areas within said separable side portions are extendable outwardly from said body structure while retaining communication with said terminal end by said signal distribution system.

11. The device of claim 1, wherein said composite and layered body structure has a pair of translayer apertures therethrough to allow for breast protrusion when said device is positioned on the precordial region of a female patient.

12. The device of claim 1, wherein said composite, layered body structure has anatomical placement reference means being disposed therein to coordinate said contact areas relative to predetermined locations on the body of a patient.

13. The device of claim 1, wherein the body structure is rectilinear and wherein said predetermined contact areas are arranged having one at each corner of the body structure and six centrally placed in the body structure to form a generally curvilinear pattern whereby said contact areas conform with standard precordial positions for "twelve-lead" electrocardiographic devices.

14. The device of claim 1, wherein said predetermined contact areas are comprised of a thin rectilinear grid configuration.

15. The device of claim 1, wherein said non-conductive base layer and said inner insulation layer are comprised of a polyester laminated material.

16. The device of claim 1, wherein said terminal end is communicatively connectable to a multi-conductive cable set of a medical diagnostic or therapeutic apparatus, said terminal end having a passive polarization means for operator identification purposes and having an active polarization means to ensure proper alignment of said terminal end for mating communication with the cable set.

17. The device of claim 1, wherein said device additionally has a flexible coextensive liner releasably affixed in surface to surface engagement to said conductive adhesive members.

18. The device of claim 1, wherein said signal distribution network is comprised of a conductive material having a predetermined conductivity to provide a current limiter through said signal distribution system.

19. A flexible, disposable electrode belt for placement on the body of a patient to receive and transmit electric current and voltage and being for use with medical diagnostic and therapeutic apparatus, said flexible and disposable electrode belt comprising:
  (a) a unitary, composite and layered main body structure with means to partially separate at least one peripheral side portion therefrom and having a terminal and a proximal end, said main body structure further having:
    (1) a non-conductive base support layer for insulation of and supporting the remaining elements of said main body,
    (2) a plurality of conductive electrodes affixed at predetermined locations on said proximal end of said non-conductive base support layer, said electrodes further having integral, elongated conductive lead strips in communication with each said electrode and being extended to the terminal end of said main body structure,
    (3) a non-conductive inner patient insulation layer affixed to and coextensive with said non-conductive base support layer and having a plurality of apertures at locations corresponding to said predetermined electrode locations and having a void at its terminal end exposing said lead strips for communicating contact, and
    (4) conductive, adhesive gel pads adhesively disposed to and being coextensive with each said aperture in said inner patient insulation layer for making contact with said electrodes and the body of a patient and for holding said device to the body of a patient; and
  (b) at least one adjustable and extendible side member defined by said separation means of said main body structure for receiving and transmitting electric current and voltage at locations outside said main body structure and having an electrode and a communicating lead strip to said terminal end of said main body structure.

20. A flexible and unitary device of a layered construction for securement to the body of a patient to receive and transmit electric current and voltage and being for use with medical therapeutic or diagnostic apparatuses comprising:
  a. a reusable, composite and layered main structure having a terminal end for mating communication with the medical apparatus, said main structure further having:
    1. a non-conductive base layer for insulation of an supporting the remaining elements of said main structure,
    2. a conduction network affixed to said base layer having a plurality of predetermined contact areas for reception and transmission of electrical signals from and to the body of a patient and a signal distribution system extending from said contact areas to said terminal end,
    3. an inner non-conductive layer affixed and coextensively disposed to said base layer for insulation of said signal distribution system from the body of a patient and having a plurality of predetermined apertures exposing said contact areas, and further having a void at said terminal end exposing said signal distribution system for communicating contact; and
  b. a disposable, composite and layered patient interface structure for coextensive mating communication with said main structure and having:
    1. a non-conductive main structure release layer having a plurality of predetermined apertures being located at positions corresponding with said predetermined apertures of said main structure inner non-conductive layer for communicating with said contact areas of said main structure, and
    2. a conductive adhesive layer coextensively disposed to said non-conductive main structure release layer for communicative contact with and between said contact areas of said main structure and the body of a patient and for releasably holding said patient interface structure to said main structure and to the body of a patient.

21. The device of claim 20, wherein said conductive adhesive layer of said patient interface structure additionally is provided with a release liner, said patient interface structure release layer further having a tab extending therefrom for allowing said conductive adhesive material layer and said release layer to be removed independently from the remaining elements of said device.

22. A unitary, disposable and flexible belt device for the releaseable securement to the body of a patient and for receiving and transmitting electric current and voltage, said device having a composite and layered body structure with a terminal end and being connectable for use with a cable set of medical therapeutic and diagnostic apparatus, said composite and layered body structure further comprising:
  a. a non-conductive base structure layer for supporting and insulating the remaining elements of said composite and layered body structure,
  b. a conduction network affixed to said non-conductive base layer having a plurality of predetermined contact areas for receiving and transmitting electrical signals and a signal distribution system extending from said contact areas to the terminal end of the device, each said contact area further having a predetermined area dimension,
  c. an inner non-conductive insulation layer affixed and coextensively disposed to said non-conductive base layer for insulating said signal distribution system from the body of a patient, said inner insulation layer having a predetermined thickness dependent upon said contact area dimension, said inner non-conductive layer further having a plurality of predetermined apertures exposing said conduction network contact areas, and having a void area at said terminal end exposing said signal distribution system, d. conductive adhesive members affixed and coextensively disposed at each said plurality of predetermined apertures of said inner insulation layer for contact with said contact areas and the body of a patient to transfer electrical signals therebetween and for holding said device to the patient, e. a conductive shielding layer generally coextensively affixed to said non-conductive base layer for reducing interference with and from the remaining elements of said body structure, and being exposed at the terminal end of said body structure for the electrical grounding of said device, said shielding layer further being peripherally recessed with respect to said non-conductive layers to minimize the risk of shorting and patient shock due to device or medical diagnostic and therapeutic apparatus malfunction, said contact area dimension, said base structure layer thickness, said shielding layer, and said conductive adhesive members cooperating to provide a low pass filter to shunt high frequency interference to ground, and, f. an anatomical reference aperture through said base structure layer, inner insulation layer and shielding layer to align said predetermined contact areas with respect to the xiphoid process of a patient.

23. A method of receiving and transmitting electric current and voltage to the body of a patient for diagnostic and therapeutic purposes comprising:

a. selecting a set of specific locations on the body of a patient to be tested or treated, b. providing an electrode belt device for placement on the body of the patient having a configuration to come into surface to surface contact with the predetermined patient body locations, said device further having a layered flexible body structure with electrode contact areas disposed at predetermined locations corresponding to said predetermined patient body locations and having at least one separable and extendible side member having an electrode contact areas therein, said belt device body structure further comprising a terminal end, a non-conductive base structure layer to which said electrode contact areas are affixed, a conduction network affixed to said base structure layer communicatively connecting said terminal end and said electrode contact areas, an inner non-conductive insulation layer affixed to and generally coextensive with said base structure layer and having apertures therein exposing said predetermined electrode contact areas, conductive adhesive members affixed and coextensively disposed at each said aperture, a release liner coextensively affixed to said conductive adhesive members, and having anatomical alignment means, c. preparing said electrode belt device for application to the body of the patient by removing said release liner from said conductive adhesive members, d. placing said electrode belt device on the body of the patient by reference to said anatomical alignment means so that said electrode contact areas correspond to said predetermined patient body locations, e. separating said side member from the body structure of the belt device and placing the electrode contact area at a predetermined location, f. connecting said terminal end of said electrode belt device to the cable set of a medical diagnostic or therapeutic apparatus, g. performing a diagnostic or therapeutic procedure by utilizing said electrode belt device in communication with said medical apparatus, and h. removing said electrode belt device from the body of the patient by pulling said electrode belt device from the skin, and disposing of said electrode belt device.

24. The method of claim 23, wherein said electrode belt device is further provided with a belt device structure wherein said adhesive conductive members are removable and disposable from the remaining elements of said device whereby subsequent to the removal of said device from the patient body only said adhesive conductive members are disposed of and the remainder of said device is reusable.

25. The method of claim 23, wherein a second electrode belt device is simultaneously used, one said device being disposed on the precordial region of the body of the patient and said second device on the dorsal surface of the patient.

26. The method of claim 23, wherein said selection of patient body locations is made to coincide with standard precordial locations for "twelve-lead" electrocardiographic applications.

* * * * *